United States Patent
Simon

[19]

[11] Patent Number: 5,762,619
[45] Date of Patent: Jun. 9, 1998

[54] FASHION BELT WITH BUILT-IN LUMBAR SUPPORT

[76] Inventor: William H. Simon, 255 S. 17th St., 11th Floor, Philadelphia, Pa. 19103

[21] Appl. No.: 798,191

[22] Filed: Dec. 9, 1996

[51] Int. Cl.⁶ .................................................. A61F 5/00
[52] U.S. Cl. ............................ 602/19; 2/312; 2/321
[58] Field of Search ................... 602/19, 36; 2/311, 2/321, 322, 338, 920, 312, 244, 245, 246

[56] References Cited

U.S. PATENT DOCUMENTS

| | | | |
|---|---|---|---|
| 756,734 | 4/1904 | Tessmer | 2/312 |
| 1,620,216 | 3/1927 | Lehr | 2/245 |
| 1,640,665 | 8/1927 | Muscente | 2/245 |
| 3,561,434 | 2/1971 | Kilbey | 602/36 |
| 3,926,183 | 12/1975 | Spiro | 602/19 |
| 4,396,012 | 8/1983 | Cobiski | 602/36 |
| 4,501,027 | 2/1985 | Olsson | 2/321 |
| 4,747,399 | 5/1988 | Glomstead | 602/36 |
| 4,776,043 | 10/1988 | Coleman | 2/244 X |
| 4,918,758 | 4/1990 | Rendina | 2/246 X |
| 5,115,802 | 5/1992 | Dyer | 602/36 X |

*Primary Examiner*—Linda C. Dvorak
*Attorney, Agent, or Firm*—McHale & Slavin

[57] ABSTRACT

A fashion belt with a built-in lumbar support. The belt employs two flexible straps, the ends of which overlap and are detachably secured to form a contiguous band that encircles and supports the lumbar region of an individual. The straps are placed in relation to each other with securement sections positionable on each side of the individual's waist. An interchangeable buckle adorns the band.

10 Claims, 2 Drawing Sheets

FASHION BELT WITH BUILT-IN LUMBAR SUPPORT

FIELD OF THE INVENTION

This device relates to belts which support the lumbar region of the spine, and more particularly to a support belt that complements wearing apparel.

BACKGROUND

Muscles in the lumbar region of the lower back are delicate and prone to injury. Injury to this area is often a result of muscle strain associated with heavy lifting. The type of lifting most likely to cause lumbar region injury is traditionally associated with involvement in athletics or industrial employment. As a result, many support devices exist which prevent lower-back injuries in these settings.

However, athletes and industry workers do not have a monopoly on lower-back pain. Office employees lift objects and engage in many back-straining activities. The inactivity of many such employees may even allow adoption of poor posture, causing lower-back pain. Unfortunately, current lumbar supports are not adapted for office settings.

Presently-known devices fall broadly into two categories: wide-banded belts and belts which place support members against an individual's lower back. Neither category is well-suited for use outside the industrial or athletic realms.

Wide-band supports are not suitable for office use. Belts in this category reduce strain on the lower back by stiffening an individual's lumbar region. However, because of the necessary force resolution involved, belts of this type must span a large portion of the body. Therefore, these belts are a major component of an individual's wearing apparel and overall appearance. Since these supports are typically designed for athletic or industrial applications, they do not fit within modern office dress codes.

Some wide-band supports place rigid bars or stays in an individual's dorsal region. Office employees may not be able to use this type of support if they sit at desks with cushion-backed chairs. Wearing a rod-reinforced support may force the rigid bar against the chair's back, causing puncture or premature wear to the chair or create an uncomfortable seating environment.

Back supports employing a flexible band to hold a support member against the lumbar region of the user are also not suitable for office use. The support forces the individual's lumbar region forward, causing the individual to lean painfully when trying to support his upper back and shoulders. This places undue strain on the muscles of the upper back. Those who wear narrow-band lumbar support in the office may ironically trade lower back pain for upper back pain.

Accordingly, what is needed is a lumbar support device that is aesthetically pleasing, so as not to interfere with an individual's appearance, allowing use in formal settings.

SUMMARY OF THE INVENTION

The present invention is a fashion belt with built-in lumbar support. The belt has an adjustable band formed from a front strap and a back strap, the ends of which overlap during use. A plurality of strap-orientation members position the back strap with respect to the front strap. Releasable fasteners are strategically positioned on each strap to secure them about the lumbar region of an individual. One of several interchangeable buckles may be detachably secured to the front strap.

An individual uses the straps to form a band which provides lower-back support. The front strap is sized to pass about an individual's abdomen, while the back strap is sized to pass about an individual's lower back. The straps cooperate to form a contiguous band which encircles an individual at approximately waist level.

In operation, an individual places the front strap horizontally against the abdomen and holds it in place. The individual then slides the ends of the back strap through orientation brackets which protrude orthogonally from the front strap. While in the orientation brackets, the ends of the back strap are secured against the inner surface of the front strap. This produces two overlapping regions, one occurring above each of the individual's hips. By varying the amount of distal-end overlap, the individual may adjust the circumference of the contiguous band to achieve a proper fit. Band circumference is correct when direct, compressive support is provided to the lumbar region. This compressive support increases intra-abdominal pressure and reduces tension on the spinal muscles. Increased abdominal pressure, in turn, reduces stress on lumbar discs and facet joints. The individual may adjust or remove the belt by separating the overlapped ends of the straps.

Vertically speaking, this type of fashion belt need not span a large portion of the individual's trunk. The belt applies constrictive pressure directly to the lumbar region of the back and it may be relatively narrow; a height of approximately three inches is sufficient. Additionally, because the belt is secured at two positions, it does not create a buildup of layers against the individual's back.

The belt is advantageously designed so that a buckle is not a load-bearing member. The buckle may be designed and placed without regard to traditionally-crucial force resolution requirements. The buckle may be attached to the front strap through frictional engagement with a mounting strap secured to the front strap.

Accordingly, it is an object of the present invention to provide a lumbar support which complements an individual's attire.

Another object of the present invention to provide a lumbar support which allows an individual to sit correctly in standard furniture without increased risk of soreness in non-lumbar-region muscles.

Still a further object of the present invention to provide a lumbar support belt having interchangeable buckles to allow one belt to be used with different attire.

Yet still a further object of the present invention to provide a lumbar support which provides concealed support, so that the support appears to be a regular belt.

It is still another object of the present intention to provide a lumbar support which is affordable, having a customizable buckle tailored to fit an individual's taste and budget.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

Figure 1:
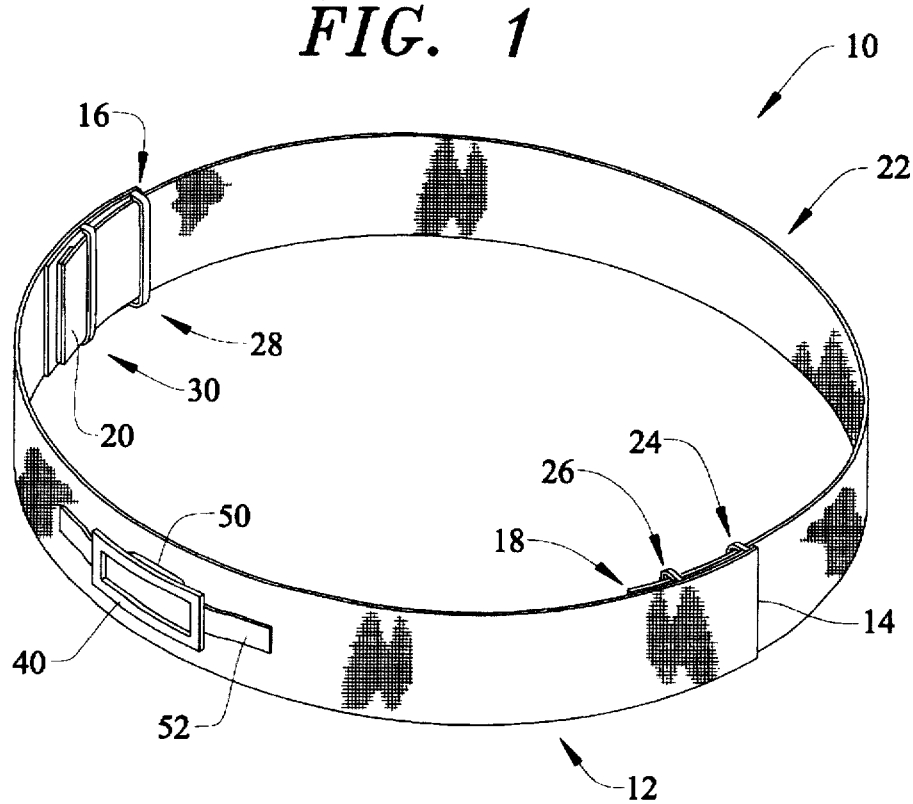
FIG. 1 is a perspective view of the device according to the present invention.
Figure 2:
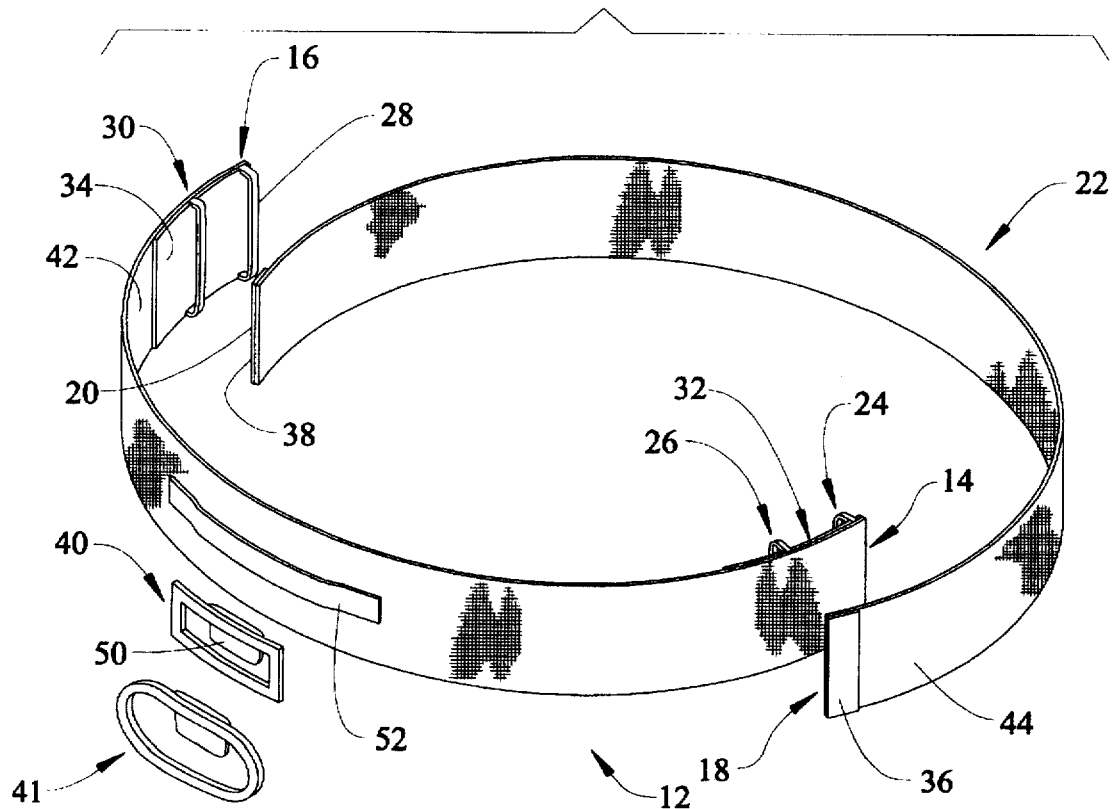
FIG. 2 is an exploded perspective view of the device according to the present invention.
Figure 3:
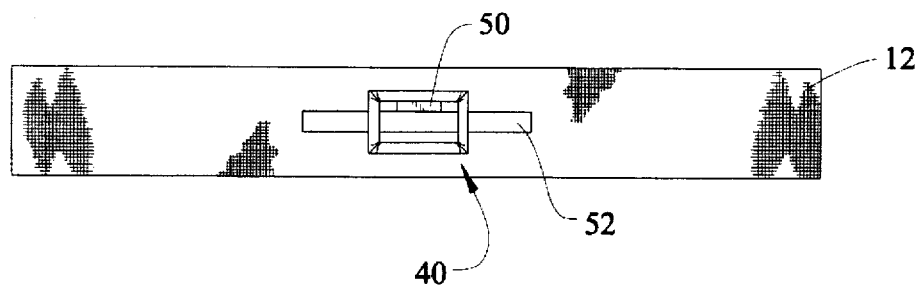
FIG. 3 is a front elevation view of the device according to the present invention.

Reference is now made to FIGS. 1 and 2, in which a preferred embodiment of the present invention 10 is illustrated. The lumbar support 10 includes a front strap 12 having a first strap end 14 and a second strap end 16, separated by a length of flexible material. First strap end 14 overlaps strap end 18 of back strap 22 and second strap end 16 overlaps a second strap end 20 of back strap 22, creating an adjustable band which encircles and supports the lumbar region of an individual. A first pair of orientation brackets 24,26 is located near the first end 14 of the front strap 12, and a second pair of orientation brackets 28,30 is located near the front strap's second end 16. A preferred relative orientation of the front strap 12 and back strap 22 is obtained by passing the first end 18 of back strap 22 through the first pair of orientation brackets 24,26, and passing the back strap's second end 20 through the second pair of orientation brackets 28,30. A first set of releasable fasteners 32,34 is located on the front strap first end 14, and front strap second end 16, respectively. This first set of releasable fasteners 32,34 couples with a second set of releasable fasteners 36,38 located, in turn, on back strap first end 18 and back strap second end 20. This coupling maintains the belt's 10 circumference during use. Additionally, one of several interchangeable buckles 40,41 frictionally engages a mounting strap 52 which is medially located on the front strap 12.

Referring in particular to FIG. 2, the front strap 12 and back strap 22 are longitudinally-extending rectangles having approximate heights between one and four inches. Both the front strap 12 and the back strap 22 are long enough to partially encircle an individual's waist. Since this belt 10 is designed to complement an individual's clothing, the straps are constructed of leather or the like materials which are used to form a belt.

In the preferred embodiment, hook and loop fastening material, known by the trademark VELCRO, is used to releasably secure the first and second ends 14,16 of front strap 12 to the first and second ends 18,20 of the back strap 22. In one orientation, releasable fasteners 32,34 contain the hook portion of a hook and loop fastener, while releasable fasteners 36,38 contain the loop portion of a hook and loop fastener. Releasable fasteners 32,34 are located on the inner surface 42 of the front strap 12, near its first and second strap ends 14,16. In these locations, releasable fasteners 32,34 are positioned to detachably mate with releasable fasteners 36,38. When mated, front strap first end 14 overlaps back strap first end 18, and front strap second end 16 overlaps back strap second end 20. The entire length of the front strap 12 and back strap 22 need not be covered with hook and loop fastening material. Placing the fastening material on the portions of the front strap 12 and back strap 22 which overlap during use is sufficient. Furthermore, the relative position of the hooks 32,34 and loops 36,38 may be reversed without negative effect.

Figure 4:
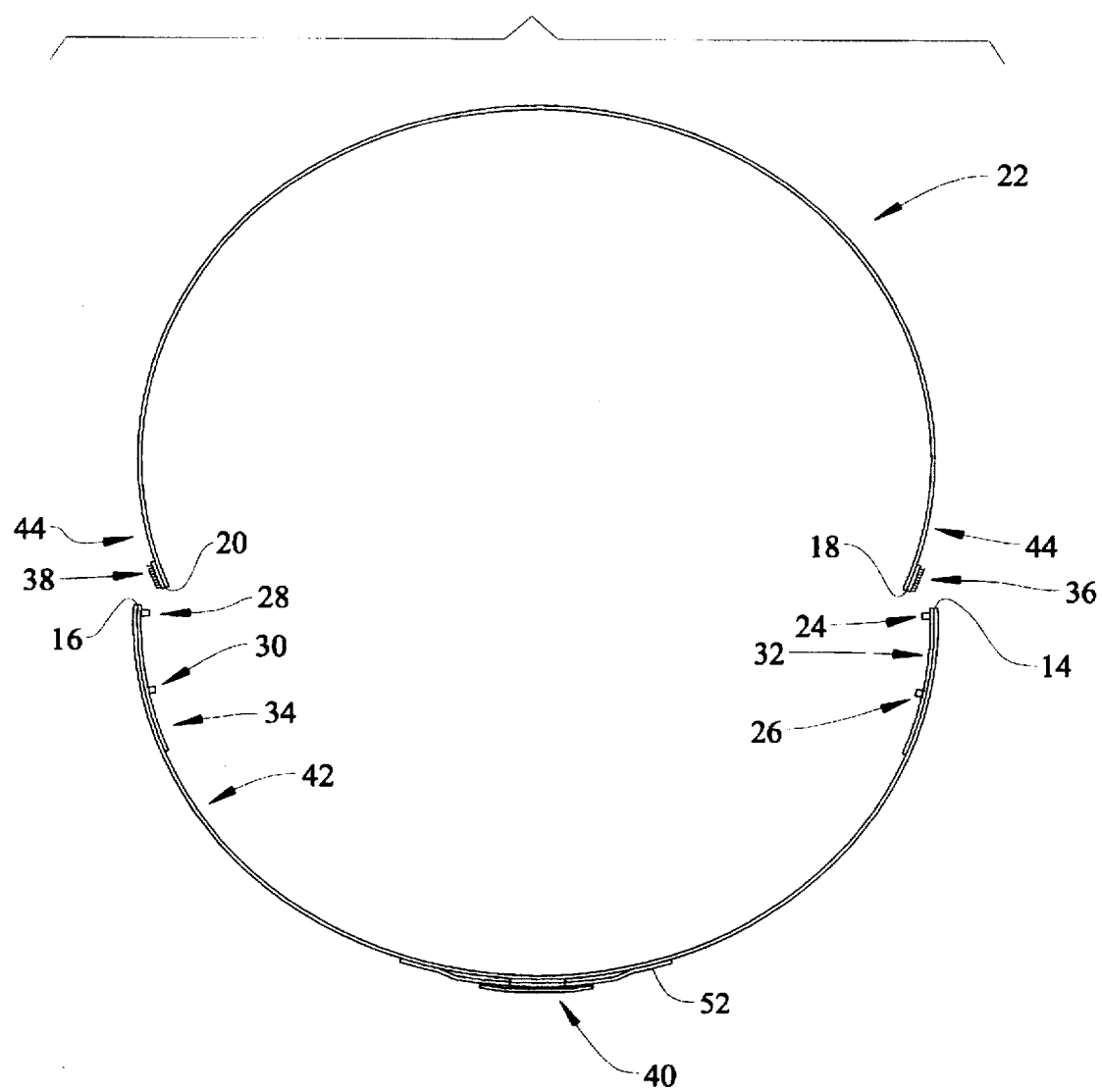
FIG. 4 is a top plane view of the device according to the present invention.

Referring to FIGS. 2 and 4, a first pair of orientation brackets 24,26 which are located on the first end 14 of the front strap 12. Ideally, bracket 24 is located at the terminal edge of the front strap's 12 first end 14, while orientation bracket 26 is located between one and three inches from bracket 24. Both brackets 26,28, which are substantially rectangular, extend radially inward toward an individual and are sized to allow sliding passage of the back strap 22 along the inner surface 42 of the front strap 12. The major axis of both brackets 26,28 are substantially perpendicular to major axis of the back strap 22. Brackets 26 and 28 may be constructed from plastic or metal.

Similarly, a second pair of orientation brackets 28,30 is located on the second end 16 of front strap 12. Preferably, bracket 28 is located at the terminal edge of the front strap's 12 second end 14, while orientation bracket 30 is located between one and three inches from bracket 28. Both brackets 28,30 which are substantially rectangular, extend radially inward toward an individual and are sized to allow sliding passage of the back strap 22 along the inner surface 42 of front strap 12. The major axis of both brackets 28,30 are substantially perpendicular to major axis of the back strap 22. Brackets 28 and 30 may be constructed from plastic or metal.

During use, the first end 18 of the back strap 22 slides through the first pair of brackets 24,26, while the second end 20 of the back strap 22 slides through the second pair of brackets 28,30. The first pair of orientation brackets 24,26 and the second pair of orientation brackets 28,30 ensure that the major axes of the front strap 12 and back strap 22 occupy parallel planes and that the muscles in the lumbar region are compressed. Once the desired circumference is obtained, the individual engages the second pair of hooks 34 and loops 38 by pressing the strap ends 14,16 against strap ends 18,20. The desired circumference is obtained when the intra-abdominal pressure is increased and tension on the spinal muscles is reduced. This increased abdominal pressure reduces stress on lumbar discs and facet joints of the individual's lower back.

Since the desired circumference is different for each individual, the belt 10 should be constructed in one of two sizes. A first size has straps 12,22 which form a band 10 that has a circumference in the range of approximately 24 inches to 40 inches. A second size has straps 12,22 which form a band 10 that has a circumference in the range of approximately 36 inches to 52 inches. In both sizes, the front strap 12 should have a height of approximately three-and-one-half inches, while the back strap 22 should have a height of approximately three-and-one-quarter inches.

Pressure may be released by disengaging the front strap first end 14 away from the back strap first end 18 and the front strap second end 16 away from back strap second end 20. The belt 10 is removed by sliding the first end 18 out of the first set of brackets 24,26 and sliding the second end 20 out from the second set of brackets 28,30.

The present invention also features an interchangeable, ornamental buckle 40. In one embodiment, the buckle is a substantially rectangular, metal ring. An L-shaped tab 50 projects from the buckle and frictionally engages a mounting strap 52 centrally disposed on the front strap 12. The major length of tab 50 slides downward, between the front strap 12 and the mounting strap 52, which has its ends sewn to the front strap 12.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What is claimed is:

1. A lumbar support belt comprising: a flexible back strap having a first end and a second end defining a length therebetween, with an inner side surface and an outer side surface; a flexible front strap having a first end and a second end defining a length therebetween, with an inner side surface and an outer side surface; a securing means for detachably securing said back strap to said front strap; a mounting strap located on said outer side surface of said front strap; a removable buckle for decorating said front strap, said buckle having an attachment tab frictionally engaging said mounting strap, whereby said front strap and said back strap cooperate to form a contiguous hoop sized to encircle the waist of an individual.

2. The lumbar support belt according to claim 1 including an orientation means which is further defined as a plurality of brackets positioned and sized to receive said first and second ends of said back strap.

3. The lumbar support belt according to claim 1, wherein said securing means includes hook-and-loop fasteners positioned on each end of said an inner side surface of said front strap and on each end of said outer side surface of said back strap, whereby said front strap is detachably secured to said back strap.

4. The lumbar support belt according to claim 1 wherein said straps are constructed from leather.

5. The lumbar support belt according to claim 1 wherein said front strap has a height of approximately three-and-one-half inches and said back strap has a height of approximately three-and one-quarter inches.

6. A lumbar support belt comprising: a flexible back strap having a first end and a second end defining a length therebetween, with an inner side surface and an outer side surface; a flexible front strap having a first end and a second end defining a length therebetween, with an inner side surface and an outer side surface; orientation means for orienting said back strap relative to said front strap; securing means for detachably securing said back strap to said front strap; and a mounting strap located on said outer side surface of said front strap; a removable buckle for decorating said front strap, said buckle having an attachment tab frictionally engaging said mounting strap, wherein said front strap and said back strap cooperate to form a contiguous hoop sized to encircle the waist of an individual.

7. The lumbar support belt according to claim 6 wherein said orientation means is further defined as a plurality of brackets projecting radially from said front strap, said brackets sized to receive said first and second ends of said back strap, whereby said first and second ends of said back strap are aligned against a said side surface of said front strap.

8. The lumbar support belt according to claim 6 wherein said securing means includes hook-and-loop fasteners positioned on said inner side surface of said front strap and said outer side surface of said back strap, whereby said front strap is detachably secured to said back strap.

9. The lumbar support belt according to claim 6 wherein said straps are constructed from leather.

10. The lumbar support belt according to claim 6 wherein said front strap has a height of approximately three-and-one-half inches and said back strap has a height of approximately three-and one-quarter inches.

\* \* \* \* \*